United States Patent
Klügl et al.

(10) Patent No.: US 6,880,528 B2
(45) Date of Patent: Apr. 19, 2005

(54) CYLINDER-HEAD-INTEGRATED DIESEL INJECTION SYSTEM WITH OIL SENSOR

(75) Inventors: Wendelin Klügl, Seubersdorf (DE); Johann Warga, Bietigheim-Bissingen (DE); Marcus Unruh, Zeitlarn (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/376,741

(22) Filed: Feb. 28, 2003

(65) Prior Publication Data

US 2004/0035398 A1 Feb. 26, 2004

(30) Foreign Application Priority Data

Apr. 18, 2002 (DE) ......................................... 102 17 383

(51) Int. Cl.[7] ............................................. F02M 55/02
(52) U.S. Cl. ....................................... 123/470; 123/468
(58) Field of Search ................................ 123/470, 468, 123/469, 446, 198 D

(56) References Cited

U.S. PATENT DOCUMENTS

| | | | |
|---|---|---|---|
| 4,168,689 A | 9/1979 | Parr | 123/139 |
| 4,348,991 A * | 9/1982 | Stang et al. | 123/41.29 |
| 4,475,498 A | 10/1984 | Hurner | 123/198 |
| 4,584,977 A | 4/1986 | Lenk et al. | 123/196 |
| 5,297,523 A * | 3/1994 | Hafner et al. | 123/456 |
| 5,604,441 A * | 2/1997 | Freese, et al. | 324/663 |
| 5,765,534 A * | 6/1998 | Brown et al. | 123/470 |
| 6,076,505 A | 6/2000 | Guggenmos et al. | 123/456 |
| 6,237,569 B1 | 5/2001 | Stelzer et al. | 123/456 |
| 6,269,796 B1 * | 8/2001 | Mitchell | 123/468 |
| 6,394,071 B1 * | 5/2002 | Nitta et al. | 123/456 |

FOREIGN PATENT DOCUMENTS

| | | | |
|---|---|---|---|
| DE | 19806595 | 2/1998 | F02M/55/02 |
| EP | 0928883 | 7/1999 | F01M/11/04 |
| JP | 10317936 | 12/1998 | F01M/11/00 |

OTHER PUBLICATIONS

"Olsensor", at internet address http://www.berlinonline.de/wissen/berlinger$_{13}$zeitung/archiv/1996/0323/ratgeber/0145, 2 pages, Mar. 23, 1996.

Fichtner, et al., "Kapazitiver Sensor zur Untersuchung von Schmierolqualitaten", at internet address http://www.htw-m.de/ks/archive/abstracts/oelsensor.html, 1 page, Mar. 17, 1998.

Siemens AG, "Functional System Design Turbocharged Diesel Engine", 1 page, Mar. 2, 2000.

Temic, "Oil Quality, Level and Temperature Sensor" at internet address http://www.temic.de, 2 pages, Dec. 2000.

Bosch Information: "Sportlich, sauber, sparsam: der Diesel mit Bosch", 1 page.

Temic, "Vorteile durch Funktionskombination bei Olsensoren", at internet address http://www.temic.de/d/nachrich/news1.asp?id=74, 1 page.

"Autoelektrik", at internet address http://www.mitglied.lycos.de/autoelektrik/Enu.htm, 2 pages.

* cited by examiner

Primary Examiner—Mahmoud Gimie
(74) Attorney, Agent, or Firm—Baker Botts L.L.P.

(57) ABSTRACT

The present invention relates to an accumulator-type injection system for injecting fuel from an accumulator into a combustion chamber of an internal combustion engine by means of injectors, the injectors being arranged completely within the cylinder head of the internal combustion engine.

9 Claims, 3 Drawing Sheets

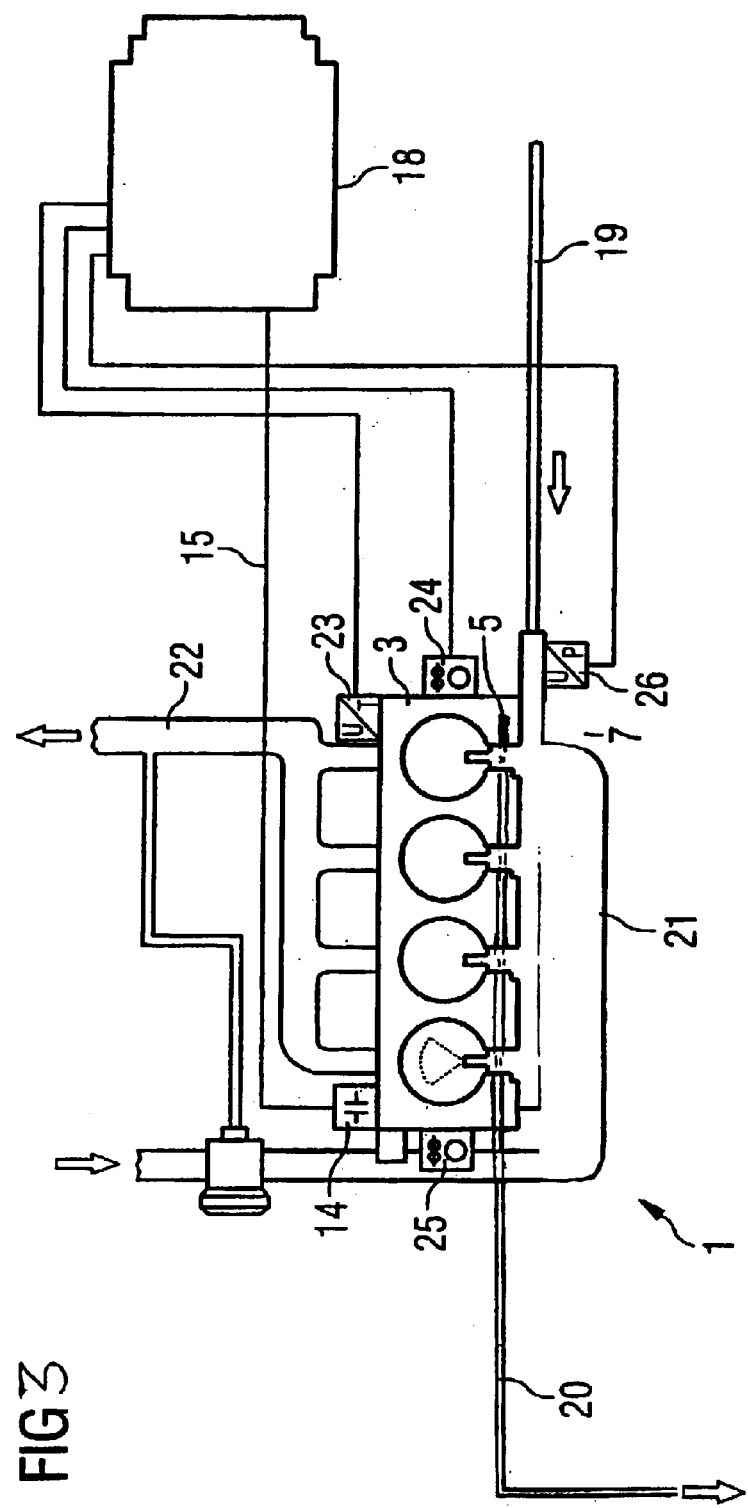

CYLINDER-HEAD-INTEGRATED DIESEL INJECTION SYSTEM WITH OIL SENSOR

CROSS-REFERENCE TO RELATED APPLICATION

This application claims foreign priority under 35 U.S.C. §119 of German application number DE10217383.4 filed Apr. 18, 2002.

TECHNICAL FIELD

The present invention relates to an accumulator-type injection system for injecting fuel.

BACKGROUND OF THE INVENTION

Accumulator-type injection systems for injecting fuel from an accumulator (rail) into a combustion chamber of an internal combustion engine using injectors are known in different embodiments. Accumulator-type injection systems have previously been constructed in such a way that the injectors are arranged outside the engine block or cylinder head and the feedlines from the rail to the injector run on the outside. As the fuel is under high pressure in the rail and in the feedlines to the injector in the accumulator-type injection systems, leakages sometimes occur, in particular at the connections between the individual components. On the one hand, this escaping fuel pollutes the environment if it drips out of the engine compartment, and on the other hand the risk of fire in the engine compartment, in which there may be relatively high temperatures, is thus increased.

Furthermore, hitherto it has not been possible in accumulator-type injection systems to sense in particular small leaks at which only small amounts of fuel penetrate to the outside. Large leaks can be determined, for example, by means of differences in the pressure in the rail. However, relatively small fuel leaks frequently evaporate at the point where they escape so that they can only be detected with difficulty, or cannot be detected at all.

SUMMARY OF THE INVENTION

The object of the present invention is therefore to make available an accumulator-type injection system which as far as possible does not give rise to contamination of the environment when there are leaks, and in which in particular even relatively small leaks can be detected This object is achieved by means of an accumulator-type injection system comprising injectors arranged completely within a cylinder head of an internal combustion engine. Preferred developments of the invention are disclosed in the subclaims.

The accumulator-type injection system according to the invention for injecting fuel from an accumulator into a combustion chamber of an internal combustion engine has the advantage that leaks at the accumulator-type injection system do not lead to pollution of the environment and no leakage escapes to the outside. This is achieved according to the invention in that the injectors are arranged completely within a cylinder head of the internal combustion engine. As a result, a leak at the injector or a feedline to the injector does not escape to the outside but rather remains in the interior of the cylinder head of the internal combustion engine in which, for example, one or more camshafts for charge cycle valves may be arranged. As the injector is arranged completely in the cylinder head, the injector is also encapsulated in the cylinder head so that a significant reduction in the injector noise is achieved. Furthermore, an improved engine design can be achieved as a particularly compact design of the internal combustion engine without the previously outwardly protruding injectors can be achieved.

According to one preferred embodiment of the present invention, the accumulator is furthermore also arranged within the cylinder head of the internal combustion engine. As a result, even greater protection against the escaping of fuel into the environment is achieved as a large number of the components of the accumulator-type injection system are arranged within the cylinder head. Furthermore, this permits a design with particularly short routing of the lines, which provides corresponding hydraulic advantages, in particular lower flow losses.

According to a further preferred embodiment of the present invention, the accumulator of the accumulator-type injection system is arranged directly on or at the cylinder head of the internal combustion engine. This arrangement also permits particularly short routing of the lines to be achieved, but in comparison with an arrangement of the accumulator in the cylinder head there is a somewhat greater risk of fuel escaping into the environment when there are leaks at the accumulator.

In order to avoid disadvantages in terms of degraded oil quality, when there is a leak in the accumulator-type injection system with the injectors or feedlines to the injectors or the rail arranged in the cylinder head of the internal combustion engine, an oil sensor which senses the quality of the engine oil is preferably provided. In fact, when there is a leak of fuel with an arrangement of one or more components of the accumulator-type injection system in the cylinder head, the fuel in the interior of the cylinder head escapes and thus contaminates the engine oil with fuel. As a result the engine oil is diluted by the fuel. The provision of an oil sensor to determine the quality of the engine oil thus makes it possible to determine a leak in the accumulator-type injection system by determining the dilution of the engine oil with fuel. As a result, serious damage to the internal combustion engine owing to diluted engine oil can be prevented.

Furthermore, an oil sensor, which senses the filling level of the engine oil, is preferably provided. As the filling level would rise when fuel leaks into the engine oil, redundant determination of a leak at the accumulator-type injection system can thus be made possible, for example. Of course, the oil sensor for the filling level can also be used in a customary way to determine the absence of engine oil. The oil sensor is particularly preferably constructed in such a way that it can simultaneously sense the quality of the engine oil and the filling level of the engine oil. As a result, only one oil sensor is necessary, permitting the design to be minimized in terms of equipment.

The oil sensor preferably senses the quality and/or the filling level of the engine oil by reference to a dielectric constant of the engine oil.

It is particularly preferred to provide a display device which can display a change in the filling level of the engine oil and/or a change in the quality of the engine oil. The signals which are output by the oil sensor are evaluated here in a control and adjustment unit and compared, for example, with values which are stored in advance, and an appropriate display is given when there is a deviation by a specific value.

The leakage line or the fuel return flow line is preferably arranged within the cylinder head, providing a particularly compact design.

The present invention is particularly preferably used in an accumulator-type injection system which is a diesel injection system.

BRIEF DESCRIPTION OF THE FIGURES

The invention is explained in more detail below with reference to the drawing, in which:

FIG. 3 is a further exemplary embodiment of an accumulator-type injection system from FIG. 2.

An exemplary embodiment of an internal combustion engine with an accumulator-type injection system according to the invention is described below with reference to FIGS. 1 and 2.

DETAILED DESCRIPTION OF THE PREFERRED EMBODIMENTS

Figure 1:
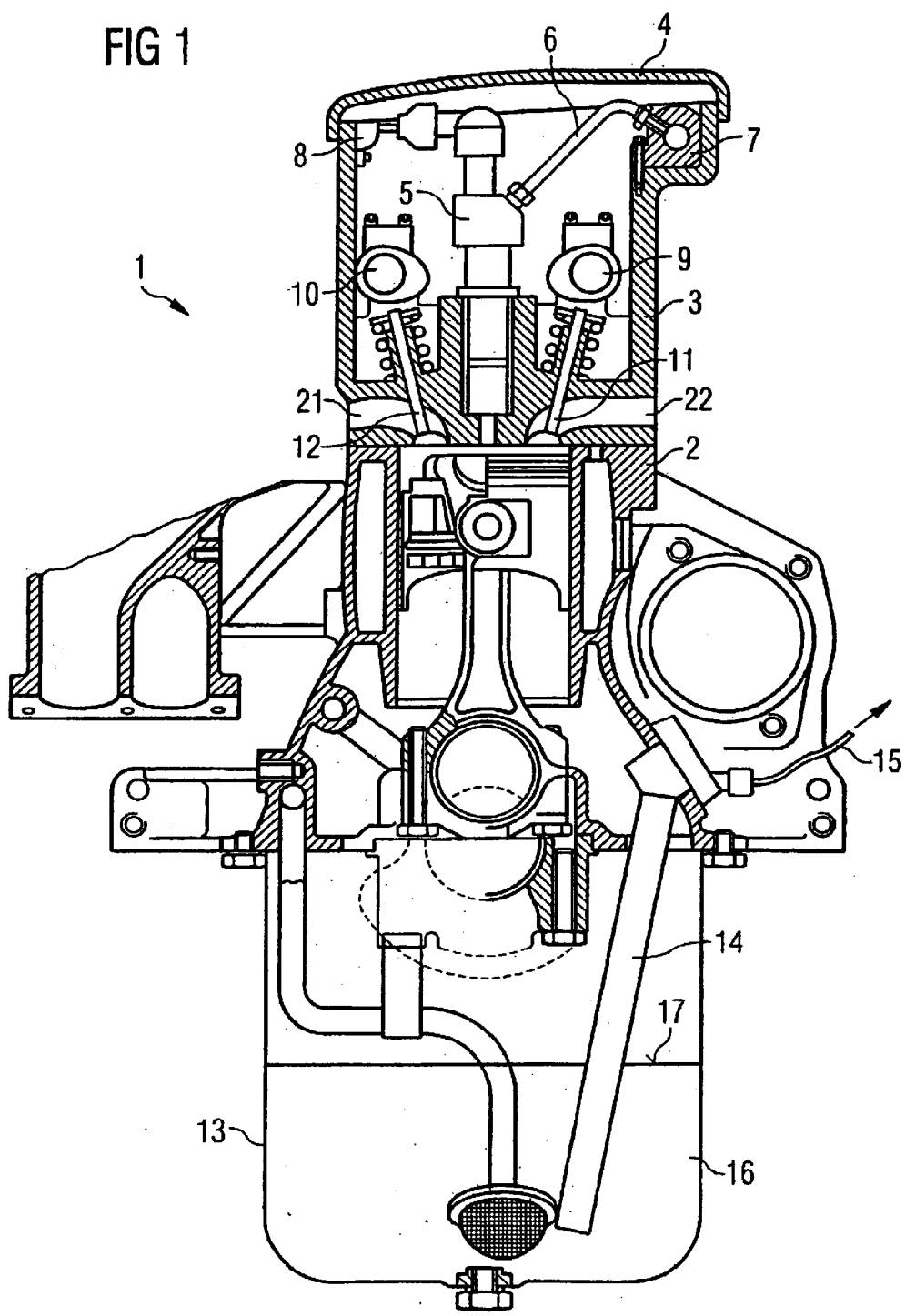
FIG. 1 is a schematic sectional view of an accumulator-type injection system integrated in the cylinder head, in accordance with an exemplary embodiment of the present invention.

As shown in FIG. 1, the internal combustion engine comprises an engine block 2 in which at least one piston together with a crankshaft is arranged in a known fashion. A cylinder head 3, which is closed off by a cylinder head cover 4, is arranged at the upper end of the engine block 2. As shown in FIG. 1, at least two charge cycle valves, namely an inlet valve 11 and an outlet valve 12, are arranged in the cylinder head 3. The inlet valve 11 is activated here by a camshaft 9, and the outlet valve 12 is activated by a camshaft 10. As is apparent from FIG. 1, the two camshafts 9, 10 are also arranged in the interior of the cylinder head 3.

As is also apparent from FIG. 1, an accumulator-type injection system, composed of an injector 5, a rail 7 and a line 6 which connects the rail 7 to the injector 5, is arranged in the cylinder head 3. The rail 7 is used in a known fashion as a fuel accumulator for storing fuel at high pressure. The injector 5 is actuated electrically by means of an electrical cable harness 8 which is also arranged in the cylinder head 3. The components of the accumulator-type injection system are arranged here in the cylinder head 3 in such a way that the functioning of the camshafts 9, 10 or of other components arranged in the cylinder head 3 is not adversely affected.

As is also apparent from FIG. 1, an oil pan 13, which has the purpose of collecting engine oil 16, is arranged in the lower region of the engine block 2. The engine oil 16 is fed in a known fashion via a filter and a line or an engine oil pump and corresponding lines to the locations in the engine which are to be lubricated, for example the pistons or the camshafts. As is illustrated in FIG. 1, an oil sensor 14 is arranged in the oil pan 13. The oil sensor 14 dips into the engine oil 16 here. The reference symbol 17 designates an oil filling level which indicates a normal oil filling level or value of the operation of the engine. The oil sensor 14 is connected via an electrical line 15 to a control and adjustment unit 18 (cf. FIG. 2). The control and adjustment unit 18 has the purpose of evaluating the signals supplied by the oil sensor 14. As is shown in FIG. 2, the control and adjustment unit 18 also receives further signals, for example from a temperature sensor 23 for the temperature of the cooling water, a crankshaft sensor 24 for the position of the crankshaft, a camshaft sensor 25 for the position of the camshafts and a pressure sensor 26 for determining the pressure in the rail.

As a result of the arrangement of the injector 5, the feed line 6 and the rail 7 in the cylinder head 3, if there is a leak in one of the components 5, 6, 7 or at the respective connecting points the leaking fuel no longer escapes outward into the environment but rather into the interior of the cylinder head 3. The leaking fuel thus passes into the lubricant circuit of the engine oil and mixes with the engine oil 16. The dilution of the engine oil with fuel which occurs can then be detected using the oil sensor 14 by means of a change in the dielectricity of the engine oil. This modified signal can then be compared, for example, with stored values in the control and adjustment unit 18 and it is thus possible to determine that the engine oil has been diluted. Furthermore, when there is a persistent leak in the accumulator-type injection system in the cylinder head 3, the oil sensor 14 can detect a rise in the oil filling level line 17 as new fuel is continuously fed into the oil circuit as a result of the leak.

The control and adjustment unit 18 can thus detect a leak in the accumulator-type injection system by means of two different signals. If appropriate, this detection can also be reconciled further with the pressure value, supplied by the pressure sensor 26, in the rail 7 of the accumulator-type injection device, even if the pressure sensor 26 can only detect a small pressure loss (when there is a small leak). The oil sensor 14 can measure the oil filling level or the quality of the engine oil by means of capacitors, for example. Here, the capacitance of the capacitors also changes with the oil filling level, or the capacitance of the capacitors also changes when there is a change in the dielectricity of the engine oil owing to the dilution with fuel. By comparing with stored values in the control and adjustment unit 18 it is also possible, for example, to detect dilution of the engine oil with water as the dielectricity of the diluted engine oil changes in a different way as a function of the fluid, i.e. fuel or water, which brings about the dilution.

If the control and adjustment unit 18 thus senses a change in the quality of the engine oil 16 or a change in the oil filling level 17, it can indicate a corresponding signal to the outside by means of a display unit and thus prevent serious damage to the engine.

The present invention is also particularly suitable for retrofitting vehicles as only one additional oil sensor 14 has to be provided and the control and adjustment unit 18 has to be correspondingly reprogrammed.

The arrangement of the injector 5, the feedline 6 and the rail 7 also provides a very compact embodiment of the internal combustion engine 1 and additionally permits a significant reduction in the injector noise as the injector is arranged in the interior of the cylinder head 3.

Furthermore, the arrangement of the accumulator-type injection system components in the cylinder head 3 makes it possible to implement very short routing of the lines with the corresponding hydraulic advantages.

Figure 2:
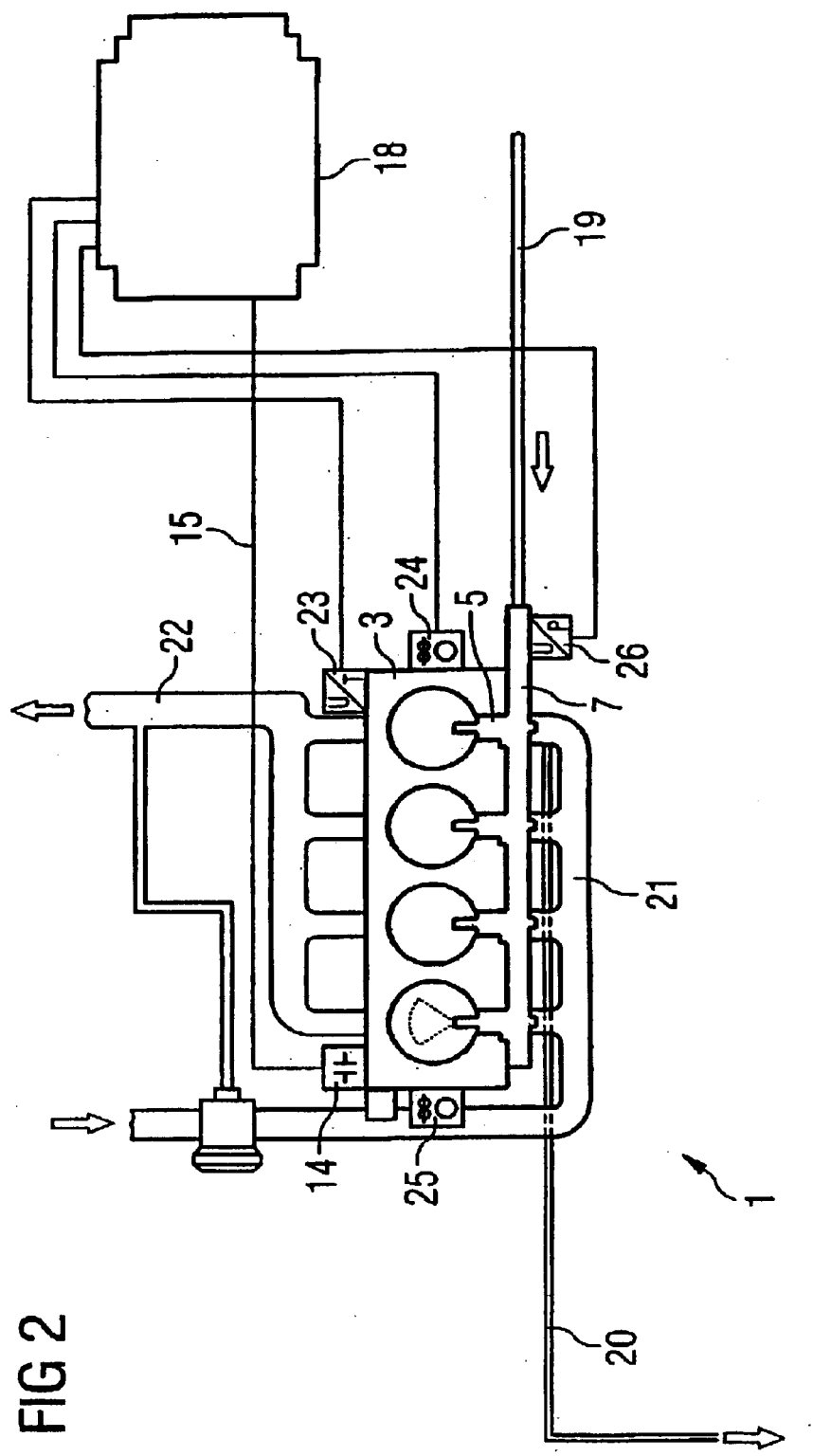
FIG. 2 is a schematic block circuit diagram of an accumulator-type injection system according to the present invention.

FIG. 2 also illustrates a high-pressure feedline 19 which feeds fuel from a high-pressure pump to the rail 7, as well as a leakage line 20 and the fuel return flow line 20 which carries away the internal leakage of the components of the accumulator-type injection system and feeds it back into the reservoir. In FIG. 2, a fresh air feedline to the internal combustion engine 1 is also designated by the reference symbol 21, and an exhaust gas line by the reference symbol 22.

FIG. 3 illustrates a further embodiment of the injection system from FIG. 2 in which the leakage line or the fuel return flow line 20 is arranged within the cylinder head 3, permitting a particularly compact design.

The present invention thus solves, in a surprisingly simple way, a number of problems which occur in particular with accumulator-type injection systems with leaks owing to a high pressure in comparison with customary injection systems, in particular for spark ignition engines. By using the oil sensor 14 it is also possible to achieve a considerable gain in safety as damage to the engine owing to unacceptable dilution of the engine oil with fuel can be prevented. Furthermore, the present invention is very well suited for retrofitting, for example in vehicles which already have a display for a lack of oil or a display for the need for a customer service oil change.

The present invention thus relates to an accumulator-type injection system for injecting fuel from an accumulator 7 into a combustion chamber of an internal combustion engine 1 by means of injectors 5, the injectors 5 being completely arranged within the cylinder head 3 of the internal combustion engine 1.

The preceding description of the exemplary embodiments according to the present invention is intended only for illustrative purposes and not for the purpose of restricting the invention. Within the scope of the invention, various changes and modifications are possible without departing from the scope of the invention and its equivalents.

What is claimed is:

1. An accumulator-type injection system for injecting fuel from an accumulator into a combustion chamber of an internal combustion engine via injectors and to detect fuel leaks, said system comprising:

injectors arranged completely within a cylinder head of the internal combustion engine; and an oil sensor to sense the quality of engine oil for determining fuel leaks.

2. The system as claimed in claim 1, wherein the accumulator is arranged within the cylinder head of the internal combustion engine.

3. The system as claimed in claim 1, wherein the accumulator is arranged directly on or at the cylinder head of the internal combustion engine.

4. The system as claimed in claim 1, wherein the oil sensor further senses a level of the engine oil.

5. The system as claimed in claim 1, wherein the oil sensor is arranged in an oil pan of the internal combustion engine.

6. The system as claimed in claim 1, wherein the oil sensor senses the dielectricity of the oil.

7. The system as claimed in claim 6 further comprising a display device for displaying a change in the dielectricity of the oil.

8. The system as claimed in claim 1 further comprising a leakage line or a fuel return flow line arranged within the cylinder head.

9. The system as claimed in claim 1, wherein the system is adapted for use in a common rail injection system for diesel engines.

* * * * *